US00PP29249P2

(12) United States Plant Patent
Deng

(10) Patent No.: US PP29,249 P2
(45) Date of Patent: Apr. 17, 2018

(54) ***CALADIUM* PLANT NAMED 'ICICLE'**

(50) Latin Name: *Caladium×hortulanum*
Varietal Denomination: Icicle

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/530,170

(22) Filed: Dec. 8, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

PUBLICATIONS

Deng, Zhanao and Harbaugh, Brent K., 'Garden White'—A Large White Fancy-leaved *Caladium* for Sunny Landscapes and Large Containers, HortScience vol. 41(3) Jun. 2006.
Goktepe, Fahrettin et al., Toward Breeding for Resistance to Fusarium Tuber Rot in *Caladium*: Inoculation Technique and Sources of Resistance, HortScience vol. 42(5) Aug. 2007.
Geraldson, C. M. et al., Combination of High Analysis Fertilizers Plastic Mulch and Fumigation for Tomato Production on Old Agricultural Land, Soil and Crop Science Society of Florida, Proceedings, vol. 25, 1965.

*Primary Examiner* — Susan McCormick Ewoldt
*Assistant Examiner* — Karen M Redden
(74) *Attorney, Agent, or Firm* — Christopher & Weisberg, P.A.

(57) ABSTRACT

A new and distinct cultivar of *Caladium* plant named 'Icicle', characterized by its mounding growth habit, numerous wide lance-type leaves that have a large white center surrounded by green margins, plants that are attractive in containers and shady landscapes, and tubers that are resistant to moderately resistant to *Fusarium solani*, the causal agent of *Fusarium* tuber rot, and spout quickly in container forcing.

5 Drawing Sheets

ACKNOWLEDGMENT OF FEDERAL RESEARCH SUPPORT

This invention was made with government support under FLA-BRA-04162 awarded by the Cooperative State Research, Education, and Extension Service, USDA and under FLA-GCR-005065 and FLA-GCR-005507 awarded by the National Institute of Food and Agriculture, USDA. The government has certain rights in the invention.

Genus and species: *Caladium×hortulanum.*
Cultivar denomination: 'Icicle'.

CROSS-REFERENCE TO RELATED APPLICATION n/a

BACKGROUND OF THE NEW CULTIVAR

The present invention relates to a new and distinct cultivar of *caladium* plant, botanically known as *Caladium×hortulanum* (referred to herein as *Caladium*), commercially referred to as a lance leaf-type *caladium* and hereinafter referred to by the name 'Icicle'.

*Caladiums* (also referred to as *Caladium* plants) are ornamental aroids frequently used as pot and landscape plants for their colorful foliage and ease of growing. The objective of the Inventor's breeding program is to create new *Caladium* cultivars that have a compact growth habit, numerous leaves, attractive foliage, and exceptional container and landscape performance.

The new *Caladium* cultivar 'Icicle' originated from a cross between 'Candidum' (commercial cultivar, not patented) and 'Gingerland' (commercial cultivar, not patented) that was made in Bradenton, Fla. in fall 2004. The new *Caladium* cultivar 'Icicle' was discovered and selected by the inventor as a single plant in Wimauma, Fla. in 2005. The new *Caladium* cultivar 'Icicle' has been found to retain its distinctive characteristics through at least 10 generations of successive asexual propagations via tuber divisions since 2006.

Plant Breeder's Rights for this cultivar have not been applied for. The new *Caladium* cultivar 'Icicle' has not been made publicly available more than one year prior to the filing of this application.

SUMMARY OF THE INVENTION

The new *Caladium* cultivar 'Icicle' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of the new *Caladium* cultivar 'Icicle' when grown under (normal or standard) horticultural practices in Wimauma, Fla. The combination of these characteristics distinguishes 'Icicle' as a new and distinct cultivar of *Caladium:*

1. symmetrical, outwardly arching and rounded plant form;
2. mounding, dense and bushy growth habit;
3. wide lance-shaped leaves that have a large white center, with dark green and grey green blotching near the margins, white midrib and primary veins, and dark green undulating borders;
4. attractive plants in containers or shady landscapes; and
5. tubers with moderate levels of resistance to *Fusarium solani*, the causal agent of *Fusarium* tuber rot.

Plants of the new *Caladium* cultivar 'Icicle' differ from plants of the female parent, 'Candidum', in the following characteristics:

1. leaves of 'Icicle' are of the lance type with the petiole attached to the base of leaves, whereas the leaves of 'Candidum' have a petiole attached to the back of the leaf (peltate); and
2. leaves of 'Icicle' have a large white center and green midrib and primary veins, whereas leaves of 'Candidum' have green midrib and primary veins.

Plants of the new *Caladium* cultivar 'Icicle' differ from plants of the male parent, 'Gingerland', in the following characteristics:

1. the leaves of 'Icicle' are larger, wider, and heart-shaped with a bright white center, whereas the leaves of 'Gingerland' are narrower and have numerous red spots; and
2. petioles of 'Icicle' are darker green with brown dashes, whereas the petioles of 'Gingerland' are plain light green.

Plants of the new *Caladium* cultivar 'Icicle' can be compared to 'White Diamond' (U.S. Plant Pat. No. 22,215). In side-by-side comparisons conducted in Wimauma, Fla., plants of the new *Caladium* cultivar 'Icicle' differ from plants of 'White Diamond' in the following characteristics:

1. plants of 'Icicle' are taller and wider than plants of 'White Diamond'; and
2. leaves of 'Icicle' are larger with a whiter center and less greyed green blotching than the leaves of 'White Diamond'.

Plants of the new *Caladium* cultivar 'Icicle' can also be compared to 'White Delight' (U.S. Plant Pat. No. 21,216). In side-by-side comparisons conducted in Wimauma, Fla., plants of the new *Caladium* cultivar 'Icicle' differ from plants of 'White Delight' in the following characteristics:

1. plants of 'Icicle' are taller and wider than plants of 'White Delight';
2. leaves of 'Icicle' are much larger and broader and have a much brighter white center than leaves of 'White Delight'; and
3. leaves of 'Icicle' are more undulated than leaves of 'White Delight'.

DESCRIPTION OF THE FIGURES

The accompanying photographs (as shown in FIGS. 1-5) illustrate the overall appearance of the new *Caladium* cultivar 'Icicle'. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
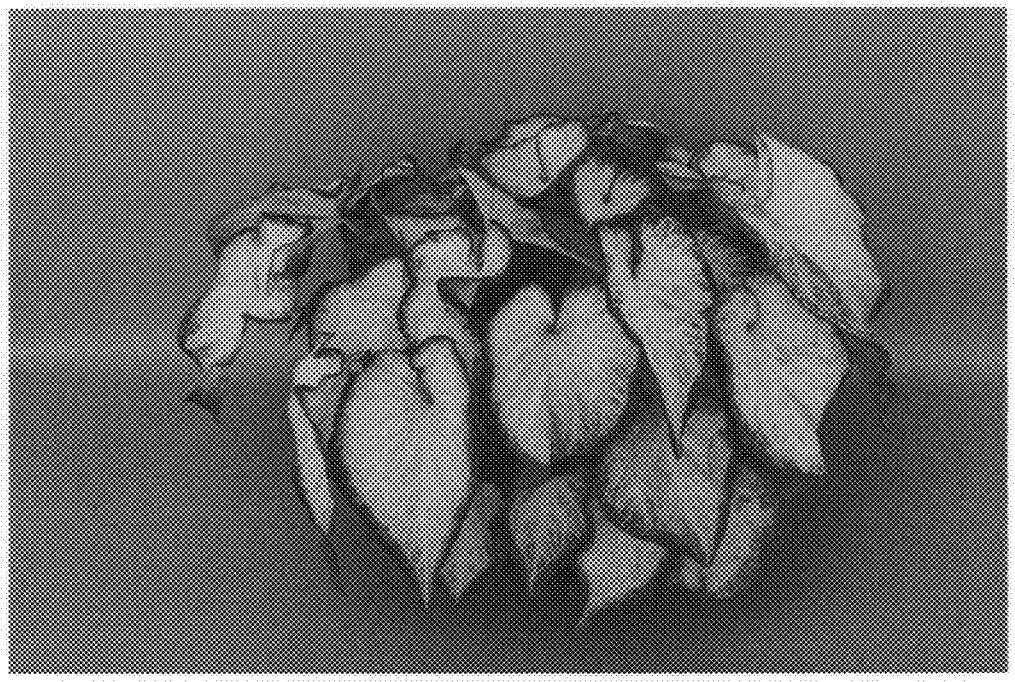
FIG. 1 shows a photograph of a side view of a typical plant of the new *Caladium* cultivar 'Icicle' grown in a 20-cm diameter container in a shadehouse.
Figure 2:
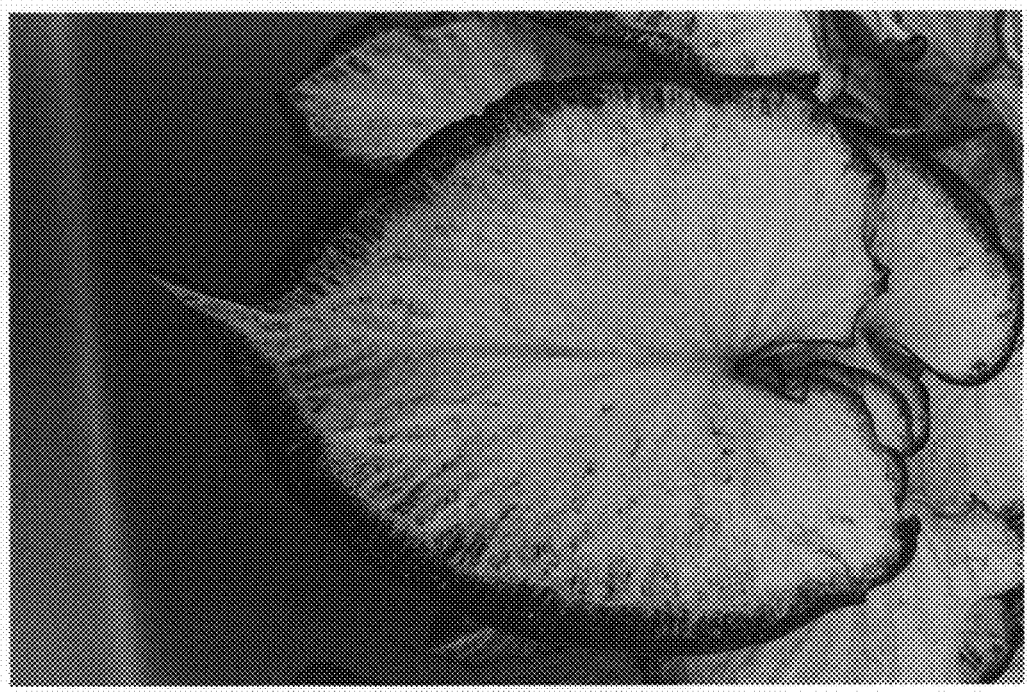
FIG. 2 shows a photograph of a top view of a typical leaf of the new *Caladium* cultivar 'Icicle' grown in a 20-cm diameter container in a shadehouse.
Figure 3:
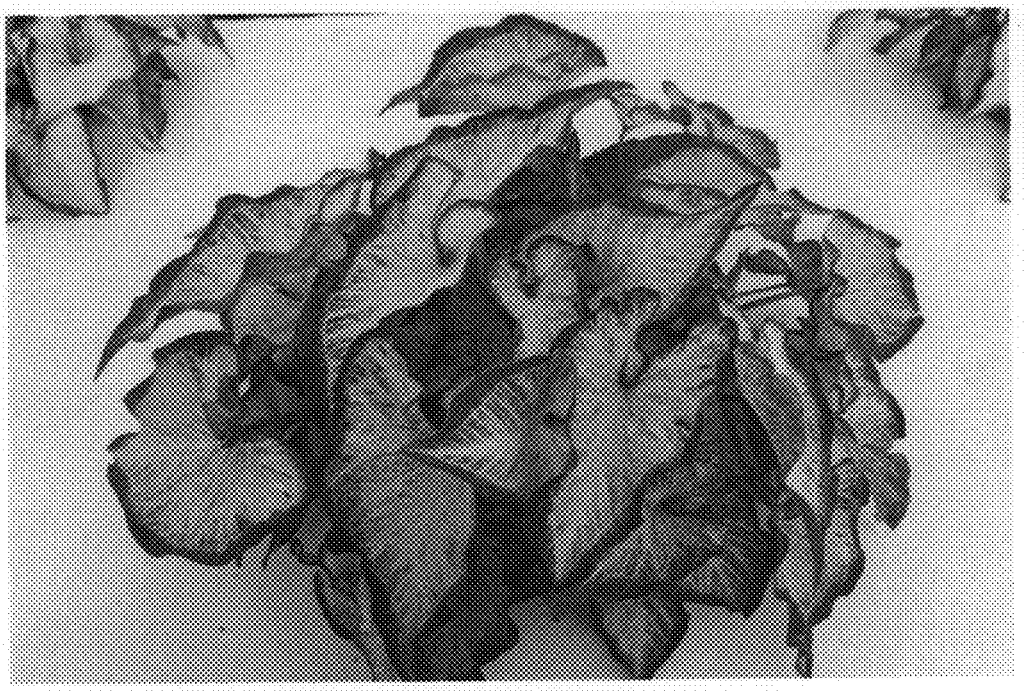
FIG. 3 shows a photograph of a top view of a typical plant of the new *Caladium* cultivar 'Icicle' grown in an outdoor nursery.
Figure 4:
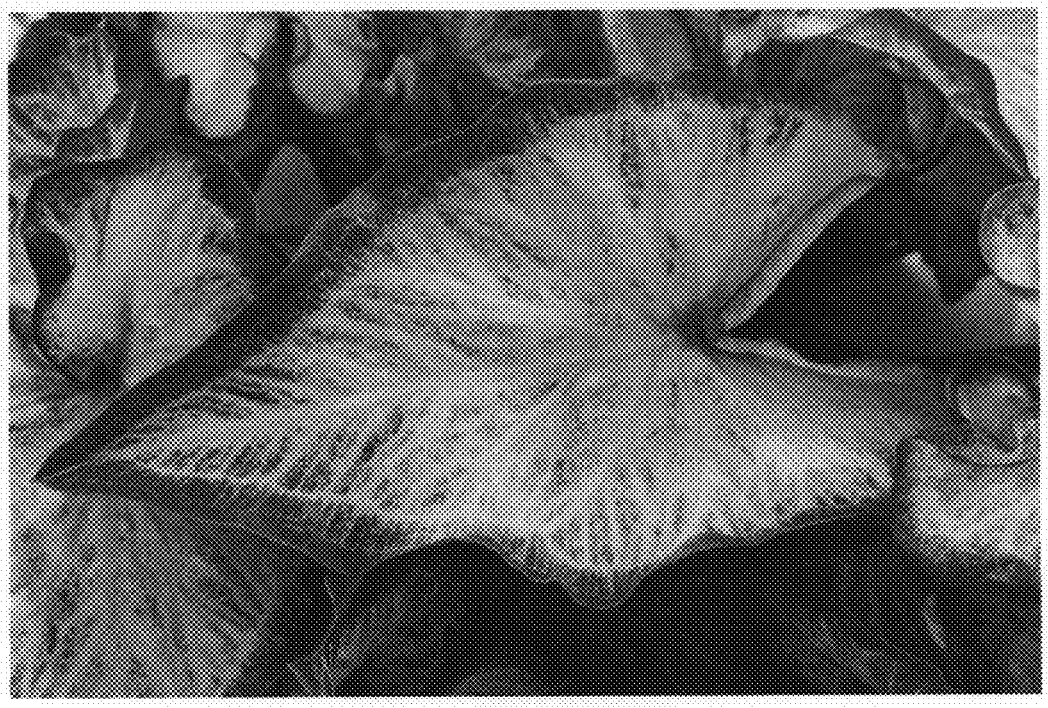
FIG. 4 shows a photograph of a top view of a typical leaf of the new *Caladium* cultivar 'Icicle' grown in an outdoor nursery.
Figure 5:
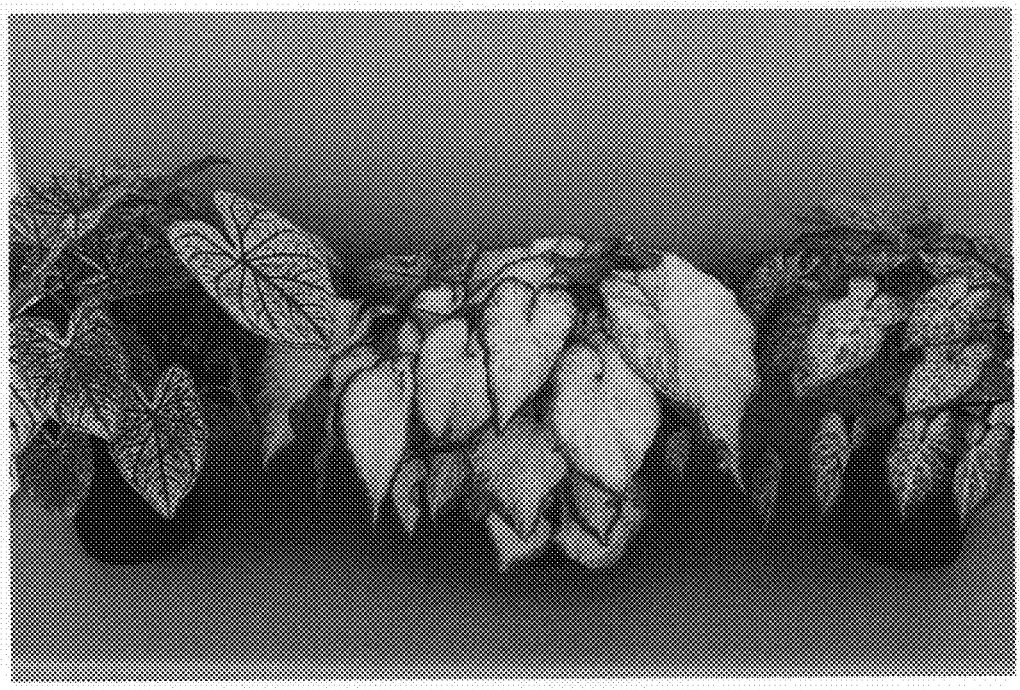
FIG. 5 shows a photograph of a side view of a typical plant of 'Candidum' (left), the new cultivar 'Icicle' (center), and 'Gingerland' (right) grown in 20-cm diameter container in a shadehouse.

In the following description, color references are made to The Royal Horticultural Society (R.H.S.) Colour Chart, 1986 Edition, except where general terms of ordinary dictionary significance are used. The features of 'Icicle' described herein are shown in FIGS. 1-5.

Description of Growing Conditions

The following observations and measurements describe plants grown in 20-cm containers in Wimauma, Fla. during the summer in a polypropylene-covered shadehouse or plants grown in outdoor ground beds in Wimauma, Fla. during the summer months. All plants were grown under conditions and practices similar to those generally used in commercial *Caladium* production.

During the production of the plants, day temperatures ranged from approximately 75° F. to 86° F., night temperatures ranged from approximately 66° F. to 76° F., and light levels were approximately 944 foot-candles in the shadehouse. Plants grown in the shadehouse were approximately eight weeks from planting tubers until when the photographs and the detailed description were taken. Plants grown in the outdoor nursery were approximately 11 weeks from planting tubers until when the photographs and the detailed descriptions were taken.

Botanical Description

Botanical classification:

*Family.*—Araceae.

*Botanical name.*—*Caladium×hortulanum.*

*Common name.*—*Caladium.*

*Cultivar.*—'Icicle'.

Parentage:

*Female or seed parent.*—'Candidum'.

*Male or pollen parent.*—'Gingerland'.

Propagation:

*Type.*—Tubers and tuber divisions.

*Time to initiate roots, summer.*—Approximately seven to ten days at 32° C.

*Time to initiate roots, winter.*—Approximately two to three weeks at 24° C.

Tuber description: Jumbo-sized tubers (approximately 6.4 to 8.9 cm in diameter) are multi-segmented, bearing six to nine dominant buds.

*Height of tubers*.—Approximately 2.5 cm to 3.3 cm.

*Diameter of tubers*.—Approximately 3.7 cm to 4 cm.

*Texture*.—Thick, starchy inside; slightly brittle between tuber segments.

*Color*.—Epidermis: Close to brown (RHS 200C). Interior: Yellow (RHS 10C).

Root description: Dense, thick and white fleshy roots.

*Color*.—White (RHS 155D).

Plant description:

*Type*.—Herbaceous perennial.

*Plant form*.—Upright, outwardly arching and symmetrical.

*Growth habit*.—Compact and mounding, dense foliage, suitable for containers with diameters of 10 cm or larger. Leaf petioles arising from tubers; petioles mostly semi-upright and curving outwardly with development.

*Plant height, from soil level to top of leaf plane, shadehouse-grown plants*.—Approximately 28.7 cm.

*Plant height, from soil level to top of inflorescences, shadehouse-grown plants*.—Approximately 33.7 cm.

*Plant spread, shadehouse-grown plants*.—Approximately 61 cm×58 cm.

*Plant height, from soil level to top of leaf plane, outdoor nursery-grown plants*.—Approximately 19.3 cm.

*Plant height, from soil level to top of inflorescences, outdoor nursery-grown plants*.—Approximately 26 cm.

*Plant spread, outdoor nursery-grown plants*.—Approximately 42 cm to 43 cm.

Foliage description (shadehouse-grown and outdoor-grown plants):

*Length, shadehouse-grown plants*.—Approximately 24.6 cm.

*Width, shadehouse-grown plants (flattened)*.—Approximately 17.5 cm.

*Length, outdoor nursery-grown plants*.—Approximately 15.3 cm.

*Width, outdoor nursery-grown plants (flattened)*.—Approximately 9.7 cm.

*Shape*.—Ovate. Apex: Acuminate to acute. Base: Cordate.

*Margin*.—Entire.

*Texture, upper surface*.—Smooth, glabrous.

*Texture, lower surface*.—Smooth, glabrous, glaucous.

*Venation pattern*.—Pinnate.

*Leaf color, shadehouse-grown plants*.—Fully expanded leaves, upper surface: Center: Close to white (RHS 155D) with blotching of green (RHS 137A) and greyed-green (RHS 191C) near the margins. Border and margins: Close to green (RHS 137A) and some leaves speckled with white (RHS 155B). Basal notch: Close to red-purple (RHS 60A) if the spot is present. Venation, midrib: Close to white (RHS 155D). Venation, primary: White (RHS 155D) to yellow-green (RHS 145C). Fully expanded leaves, lower surface: Center: Close to white (RHS 155D) with blotching of green (RHS 137C near the margins. Border and margins: Close to greyed-green (RHS 191A). Basal notch: Close to greyed-purple (RHS 187B). Venation, midrib: Close to white (RHS 155A). Venation, primary: Close to white (RHS 155A). Some veins have a narrow line of yellow-green (RHS 144B or 144C) running down the center.

*Leaf color, outdoor nursery-grown plants*.—Developing leaves, upper surface: Center: Close to white (RHS 155B), with blotching of green (RHS 137A) and greyed-green (RHS 194C) mainly near the borders. Border and margins: Close to green (RHS 137A). Basal notch: Close to red-purple (RHS 60A) at sinus cavity. Venation, midrib: Close to greyed-green (RHS 190C). Venation, primary: Close to greyed-green (RHS 194B). Developing leaves, lower surface: Center: Close to white (RHS 155D), with blotches of yellow-green (RHS 146A to 146C). Border and margins: Close to greyed-green (RHS 191A). Venation, midrib: Close to yellow-green (RHS 145C). Venation, primary: Close to yellow-green (RHS 145A). Fully expanded leaves, upper surface: Center: Close to white (RHS 155A), with blotches of green (RHS 137A) and greyed-green (RHS 191C) throughout the leaf surface. Border and margins: Close to green (RHS 137A). Basal notch: Close to red-purple (RHS 60B) on sinus cavity. Venation, midrib: Close to white (RHS 155D). Venation, primary: Close to green-white (RHS 157B). Fully expanded leaves, lower surface: Center: Close to white (RHS 155D), with greyed-green (RHS 191A and 191B) throughout the interior of the leaf surface. Border and margins: Close to greyed-green (RHS 191A). Venation, midrib: Close to yellow-green (RHS 145C). Venation, primary: Close to yellow-green (RHS 145A and 145B).

*Petiole*.—Aspect: Mostly erect, curving outward with development. Strength: Strong, flexible. Shadehouse-grown plants: Length: Approximately 23-28 cm. Diameter, distal: Approximately 4.8 mm. Diameter, proximal: Approximately 9.2 mm. Color: Close to greyed-green (RHS 196B) to yellow-green (RHS 144C) with numerous streaks of black (RHS 202A) near the proximal end. Wing length: Approximately 6.0-8.0 cm. Wing diameter: Approximately 5.0-9.0 mm. Wing color: Close to yellow-green (RHS 144B) with streaks of black (RHS 202A). Outdoor nursery-grown plants: Length: Approximately 14-19 cm. Diameter, distal: Approximately 3.5 mm. Diameter, proximal: Approximately 6.0 mm. Color: Close to yellow-green (RHS 145A) at the distal end and close to yellow-green (RHS 144A and 144B) toward the proximal end. Spots of red-purple (RHS 60A) are occasionally seen at the basal notch. Wing length: Approximately 4.5-6.0 cm. Wing diameter: Approximately 4.2-6.7 mm. Wing color: Close to white (RHS 155B) with short streaks of yellow-green (RHS 147A) throughout the wing length.

Inflorescence description: Plants of 'Icicle' under natural conditions produce inflorescences only occasionally.

*Inflorescence arrangement*.—Upright hooded spathes surrounding a columnar spadix borne on an upright scape. Spadix carries sessile, simple female and male flowers separated into two zones. Female flowers are arranged on the lower one-third of the spadix and male flowers are arranged on the upper two-thirds of the spadix. Sterile flowers develop between female and male flower zones. Spadix constricts near the sterile flower zone.

*Fragrance*.—None detected.

*Natural flowering season/longevity*.—Plants of 'Icicle' typically flower during spring or summer in central Florida. Flowers develop about two to seven weeks after growth commences. Inflorescences last about four days before fading.

*Spathe*.—Length: Approximately 12.2 cm. Width: Distal: Approximately 2.2 cm. Proximal: Approximately 3.2 cm. Shape: Ovate to somewhat obovate. Apex: Acute to acuminate. Base: Tapering. Margin: Entire. Texture, upper and lower surfaces: Smooth, glabrous. Color, front surface: Upper two-thirds: Close to white (RHS 155A). Lower one-third: Close to green (RHS 143C) to yellow-green (RHS 145D) and dashes of brown (RHS 200D) but lighter. Color, rear surface: Upper two-thirds: Close to white (RHS 155A) and blotches of yellow-green (RHS 144C or 146D). Lower one-third: Close to green (RHS 143C) and streaks of yellow-green (RHS 145D).

*Spadix*.—Length, entire spadix: Approximately 8.5 cm. Length, male flower zone: Approximately 4.1 cm. Length, sterile flower zone: Approximately 1.7 cm. Length, female flower zone: Approximately 1.0 cm. Diameter, male flower zone: Approximately 9.5 mm. Diameter, sterile flower zone: Approximately 5.2 mm. Diameter, female flower zone: Approximately 8.0 mm. Shape: Spindle-shaped to columnar. Apex: Obtuse. Base: Obtuse. Aspect: Upright. Color, mature, male zone: Close to yellow-white (RHS 158A and 158B). Color, mature, sterile zone: Close to yellow (RHS 155D). Color, mature, female zone: Close to greyed-yellow (RHS 162A). Male flowers: Quantity per spadix: Approximately 225. Shape: Obovate. Height: Approximately 3.2 mm. Diameter: Approximately 3.5 mm. Pollen color: Close to yellow-white (RHS 158B). Amount of pollen: Scant. Female flowers: Quantity per spadix: Approximately 48. Shape: Obovate. Height: Approximately 9.9 mm. Diameter: Approximately 2.5 mm.

*Scape*.—Length: Approximately 21.3 cm. Diameter: Approximately 6.1 mm. Strength: Sturdy, flexible. Aspect: Erect, upright, but with some arching. Texture: Smooth, glabrous, glaucous. Color: Proximal: Close to green (RHS 137C). Just below spathe: Close to green (RHS 138C).

Seed and fruit: Seed and fruit development has not been observed on inflorescences that were not hand-pollinated.

Disease/pest resistance: Tubers of the new *Caladium* cultivar 'Icicle' are resistant to moderately resistant to *Fusarium solani*, the causal agent of *Fusarium* tuber rot.

Temperature tolerance: Tolerant to temperatures ranging from approximately 7° C. to approximately 40° C.

Sunburn tolerance: Moderate levels of tolerance to sunburns.

Comparison with Known Cultivars

The new *Caladium* cultivar 'Icicle' was evaluated for tuber production and plant performance at the in Balm, Fla. in 2010 and 2014. The soil was EauGallie fine sand with about 1% organic matter and a pH between 6.2 and 7.4. *Caladium* plants were grown in the field using a plastic-mulched raised-bed system. In the 2010 season, ground beds (81 cm wide, 20 cm high) were fumigated on March 21 with a mixture of 80% methyl bromide and 20% chloropicrin (by volume) at 196 $kg \cdot ha^{-1}$. *Caladium* seed pieces (tuber pieces, approximately 2.5×2.5×2.5 cm) were planted manually on April 9 with approximately 25.4 cm between-row spacing and approximately 15.2 cm in-row spacing. Irrigation was through a seepage system (Geraldson et al., 1965), which maintained a relatively consistent water table below the covered beds. Two teaspoons (approximately 14 grams) of the controlled-release fertilizer OSMOCOTE® (15N-2.6P-10K, 8-9 months) was applied to each plant on 18 May, 2010. One additional teaspoon (approximately seven grams) of the controlled-release fertilizer OSMOCOTE® was applied on Aug. 13, 2010. New crop tubers were dug, washed, and dried in December 3 to Dec. 6, 2010. Dried tubers from each experimental field plot were weighed, graded, and counted in mid-January 2011, as described by Deng and Harbaugh (2006). Tuber grading was by the maximum diameter: Super Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a production index to show the relative economic value of the harvested tubers per field plot: Production index=8n (Supper Mammoth)+6n (Mammoth)+4n (Jumbo)+2n (No.1)+1n (No.2), where n=number of tubers in the grade. The relative values assigned to the five tuber grades in calculating production index were based on the relative market prices provided by Florida *caladium* tuber producers.

For the 2014 evaluation, beds were fumigated on January 9 with the soil fumigant PIC-CLOR 60® (39.0% 1,3-dichloropropene and 59.6% chloropicrin) at 448 $kg \cdot ha^{-1}$. The controlled-release fertilizer PLANTACOTE® Pluss (14N-3.9P-12.5K, 12 months, X-Calibur Plant Health Company, LLC, Summerville, S.C.) was incorporated into the bed at 336 $kg \cdot ha^{-1}$. *Caladium* seed pieces were planted on April 26 at approximately 15-cm spacing between rows and in rows. Irrigation was by seepage as described by Geraldson et al. (1965). *Caladium* plants were fertilized with 600 ppm of nitrogen with a commercial water-soluble fertilizer (20N-8.7P-16.6K, Southern Agricultural Insecticides, Inc., Palmetto, Fla.) on September 18 and Oct. 1, 2014. Tubers were dug from December 1 to Dec. 9, 2014, followed by the same washing, drying, weighing, grading, and counting procedures as were done in 2010.

In both seasons, field plots were arranged in a randomized complete block design with three replicates. The plot size in the 2010 season was 0.8 $m^2$ and was planted with 21 *Caladium* propagules, which the plot size in the 2014 season was 1.2 $m^2$ and was planted with 30 *Caladium* propagules (tuber pieces). The commercial cultivar 'Florida White Ruffles' (U.S. Plant Pat. No. 14,402) or 'White Wing' (commercial cultivar, not patented) was included in the field as checks to assess the tuber yield and plant performance of the new cultivar 'Icicle'. Analysis of variance was conducted using the JMP Pro 12 program, followed by pairwise mean comparisons using the least significant difference (LSD) (The SAS Institute, Inc., Cary, N.C., 2016). Tuber grade distribution data were transformed using the arcsine function in Excel {asin [sqrt (tuber grade distribution in percentage/100)]}. Mean values with the same letters within columns by year in Table 1 are not significantly different at $P<0.05$.

Table 1 shows the tuber weight, marketable tubers, production index, and grade distribution of the new *Caladium* cultivar 'Icicle' grown in Wimauma, Fla. in 2010 and 2014. Values presented for each year are means of three plots in three randomized complete blocks.

TABLE 1

| Cultivars | Year | Tuber Weight (kg) | Tuber Marketable (no.) | Tuber Production index[z] |
|---|---|---|---|---|
| 'Icicle' | 2010 | 2.29 a | 28.0[NS] | 81.3 a |
| 'Florida White Ruffles' | 2010 | 1.15 b | 19.0 | 41.7 b |
| 'Icicle' | 2014 | 1.82[NS] | 36.3[NS] | 71.3[NS] |
| 'White Wing' | 2014 | 1.99 | 29.7 | 62.3 |

| Cultivars | Year | Tuber grade distribution (%) Mammoth | Jumbo | No. 1 | No. 2 |
|---|---|---|---|---|---|
| 'Icicle' | 2010 | 9.7 a | 34.8[NS] | 39.1[NS] | 16.3[NS] |
| 'Florida White Ruffles' | 2010 | 0.0 b | 20.6 | 49.4 | 30.0 |
| 'Icicle' | 2014 | | 14.1[NS] | 52.7[NS] | 33.1[NS] |
| 'White Wing' | 2014 | | 16.9 | 56.8 | 26.3 |

[NS]Not significantly different at P < 0.05.

As shown in Table 1, the tuber weight and production index of the new cultivar 'Icicle' in 2010 was 2.29 kg and 81.3, respectively, which were 95.0% to 99.0% greater than the tuber weight or production index of 'Florida White Ruffles'. In the 2014 season, the new cultivar 'Icicle' and 'White Wing' did not show significant differences in tuber weight, marketable number, and production index. There were no significant differences in tuber grade distribution between the new cultivar and 'Florida White Ruffles' or 'White Wing', except that the new cultivar 'Icicle' produced more Mammoth-sized tubers than 'Florida White Ruffles'.

Table 2 shows a comparison of plant height, number of leaves, leaf length, and leaf width of the new cultivar 'Icicle' with 'Florida White Ruffles' approximately four months after planting 2.5-cm tuber pieces (propagules) in ground beds in full sun in 2010 and with 'White Wing' in 2014. Plant height, number of leaves per plant, and leaf size (maximum length and width) were measured on three plants arbitrarily chosen from each plot, approximately four months after planting. Leaf length was measured on the largest leaves along the longest line from the leaf lobe to the leaf tip. Leaf width was measured on the largest leaves across the widest middle part.

Values presented are means of data from three replications and three plants measured per plot per year. Mean values with the same letters within columns are not significantly different at P<0.05.

TABLE 2

| Cultivars | Year | Plant height (cm) | Leaves (no.) | Leaf length (cm) | Leaf width (cm) |
|---|---|---|---|---|---|
| 'Icicle' | 2010 | 37.2 a | 32.1[NS] | 22.1 a | 12.6 a |
| 'Florida White Ruffles' | 2010 | 15.5 b | 32.3 | 13.9 b | 6.0 b |
| 'Icicle' | 2014 | 23.5[NS] | 20.3 a | 18.9[NS] | 11.2[NS] |
| 'White Wing' | 2014 | 28.5 | 9.8 b | 20.0 | 11.5 |

NS = Not significantly different at P < 0.05.

As shown in Table 2, plants of the new cultivar 'Icicle' grown in the ground beds had an average height of 37.2 cm, 21.7 cm taller than 'Florida White Ruffles'. Leaves of the new cultivar 'Icicle' were 22.1 cm long and 12.6 wide, significantly longer and wider than the leaves of 'Florida White Ruffles'. Plants of the new cultivar 'Icicle' had an average of 20.3 leaves per plant, approximately 107% more than the number of leaves 'White Wing' plants produced.

Table 3 shows the landscape performance of the new cultivar 'Icicle' with 'Florida White Ruffles' when planted in ground beds in full sun in 2010 and with 'White Wing' in 2014. Values presented are means of three replications in each year. Mean values followed by the same letter in the columns of Table 3 are not significantly different by the least significant difference test at P<0.05.

The landscape performance of the new cultivar 'Icicle' was evaluated on the same plots used for evaluating tuber production. A scale of 1 to 5 was used with 1 being very poor (few leaves and lack of vigor) and 5 being excellent (full plants, numerous leaves, and bright color display). Evaluations of plant performance were done in July, August, September, and October 2010, and July, August, September, and October in 2014.

As shown in Table 3, the new cultivar 'Icicle' performed relatively well in both 2010 and 2014 growing seasons, with performance ratings between 2.9 and 4.5 in 2010 and between 3.0 and 3.8 in 2014. Its performance ratings were significantly higher than those of 'Florida White Ruffles' (2.3 to 2.8) in three evaluations in 2010.

TABLE 3

| Cultivars | 2010 July | August | September | October |
|---|---|---|---|---|
| 'Icicle' | 2.9[NS] | 3.9 a | 4.3 a | 4.5 a |
| 'Florida White Ruffles' | 2.3 | 2.8 b | 2.7 b | 3.0 b |
| 'White Wing' | — | — | — | — |

| Cultivars | 2014 July | August | September | October |
|---|---|---|---|---|
| 'Icicle' | 3.0[NS] | 3.5[NS] | 38[NS] | 3.7[NS] |
| 'Florida White Ruffles' | — | — | — | — |
| 'White Wing' | 3.2 | 3.3 | 3.3 | 3.2 |

[NS]Not significantly different at P < 0.05.

Table 4 shows the sunburn tolerance of the new cultivar 'Icicle' with 'Florida White Ruffles' when planted in ground beds in full sun in 2010 and with 'White Wing' in 2014. Values presented are means of three replications in each year. Mean values with the same letters within columns are not significantly different at P<0.05.

Leaf sunburn tolerance of the new cultivar was evaluated on the same plots used for evaluating tuber production. Leaf sunburn tolerance was evaluated on a scale of 1 to 5, with 1 being very susceptible to sunburn (leaves having numerous sun-damaged areas or holes) and 5 being resistant to sunburn (no visible sun-damaged areas). Evaluations of plant performance and sunburn tolerance were done in July, August, September, and October 2010, and July, August, September, and October in 2014.

As shown in Table 4, the new cultivar 'Icicle' showed a moderate level of sunburn tolerance in the 2010 and 2014 growing seasons, with sunburn tolerance ratings between 2.6 and 3.9. Its sunburn tolerance ratings were higher than those of 'Florida White Ruffles' (3.3 to 3.8) in one evaluation, but lower than those of 'White Wing' (3.3 to 4.3) in one evaluation.

TABLE 4

| Cultivars | 2010 July | 2010 August | 2010 September | 2010 October |
|---|---|---|---|---|
| 'Icicle' | 3.3$^{NS}$ | 3.7$^{NS}$ | 3.9 a | 3.6$^{NS}$ |
| 'Florida White Ruffles' | 3.3 | 3.8 | 3.3 b | 3.3 |
| 'White Wing' | — | — | — | — |

| Cultivars | 2014 July | 2014 August | 2014 September | 2014 October |
|---|---|---|---|---|
| 'Icicle' | 3.6 b | 3.3$^{NS}$ | 3.7$^{NS}$ | 2.6$^{NS}$ |
| 'Florida White Ruffles' | — | — | — | — |
| 'White Wing' | 4.3 a | 3.8 | 3.4 | 3.3 |

$^{NS}$Not significantly different at $P < 0.05$.

The suitability of the new cultivar 'Icicle' for pot plant production was evaluated by forcing tubers in 11.4-cm containers (diameter) in spring 2012. No. 1 tubers were planted on April 13 in a commercial potting mix (Fafard 3B) amended with the controlled-release fertilizer OSMOCOTE® (15N-3.9P-10K, 5-6 months) at 4.3 kg·m-3; plants were grown in a greenhouse with approximately 30% light exclusion. Temperatures in the greenhouse ranged from 16° C. (night) to 30° C. (day). Potted plants were arranged on metal benches in the greenhouse in a randomized complete block design with seven replicates. The number of days from planting to the first unfurled leaf was recorded as days to sprout. Plant height, plant width, number of leaves, and foliar characteristics were recorded on Jun. 11, 2012, about eight weeks after planting. Quality of the potted *Caladium* plants was rated on a scale of 1 to 5, with 1=very poor, unattractive, totally unacceptable as potted plants with few leaves, and 5=very attractive, full plants with a symmetrical shape, an appropriate height, and many bright, colorful leaves.

Table 5 shows a comparison of number of days to sprout, plant height, plant width, leaf number, leaf length, leaf width, and quality rating of the new cultivar 'Icicle' with 'Florida White Ruffles' and 'White Wing' when intact or de-eyed No. 1 (3.8 to 6.4 cm in diameter) tubers were planted individually in containers. Mean values with the same letters within columns are not significantly different at $P<0.05$.

TABLE 5

| Cultivar | Days to sprout Intact | Days to sprout De-eye | Plant height Intact | Plant height De-eye | Plant width Intact | Plant width De-eye |
|---|---|---|---|---|---|---|
| 'Icicle' | 19.0 b | 20.4 b | 26.1 a | 24.0 b | 39.6$^{NS}$ | 36.9$^{NS}$ |
| 'Florida White Ruffles' | 27.9 a | 26.0 a | 22.3 b | 17.6 c | 42.7 | 35.8 |
| 'White Wing' | 25.4 a | 27.1 a | 28.7 a | 28.7 a | 39.4 | 37.6 |

| Cultivar | Leaves (no.) Intact | Leaves (no.) De-eye | Leaf length Intact | Leaf length De-eye | Leaf width Intact | Leaf width De-eye |
|---|---|---|---|---|---|---|
| 'Icicle' | 23.4 a | 57.1 a | 22.5 a | 15.4 a | 15.2 a | 9.7 a |
| 'Florida White Ruffles' | 31.6 a | 63.4 a | 16.5 b | 12.6 b | 9.4 c | 6.8 b |
| 'White Wing' | 13.3 b | 29.3 b | 21.7 a | 16.4 a | 12.9 b | 7.8 b |

TABLE 5-continued

| Cultivar | Blooms (no.) Intact | Blooms (no.) De-eye | Quality rating Intact | Quality rating De-eye |
|---|---|---|---|---|
| 'Icicle' | 0.7 b | 0.0$^{NS}$ | 4.0 a | 4.6$^{NS}$ |
| 'Florida White Ruffles' | 0.4 b | 0.0 | 3.2 b | 4.2 |
| 'White Wing' | 1.7 a | 0.3 | 2.7 b | 4.1 |

$^{NS}$Not significantly different at $P < 0.05$.

As shown in Table 5, intact tubers of the new cultivar 'Icicle' sprouted 19 days after planting, approximately six to nine days earlier than those of 'Florida White Ruffles' or 'White Wing'. Plants of the new cultivar 'Icicle' from the intact tubers had an average height and width of 26.1 and 39.6 cm, 3.8 cm taller than plants of 'Florida White Ruffles', but were not significantly different from plants of 'White Wing' in height and width. Plants of the new cultivar 'Icicle' produced much longer (by 36.4%) and wider (by 61.7%) leaves than plants of 'Florida White Ruffles'. The former also received a higher quality rating (4.0 vs. 3.2). Plants of the new cultivar 'Icicle' produced 75.9% more leaves than plants of 'White Wing', and leaves of the new cultivar were 2.3 cm wider than leaves of 'White Wing'. Plants of the new cultivar 'Icicle' were of much higher quality than those of 'White Wing' (4.0 vs. 2.7).

De-eyed tubers of the new cultivar 'Icicle' sprouted in approximately 20 days after planting, five to seven days earlier than 'Florida White Ruffles' or 'White Wing'. On average, plants of the new cultivar 'Icicle' forced from de-eyed tubers were 24.0 cm high and 36.9 cm wide, which were intermediate between 'Florida White Ruffles' and 'White Wing'. De-eyed plants of the new cultivar were significantly different from de-eyed 'Florida White Ruffles' in that the former had 22.2% longer and 42.6% wider leaves. De-eyed plants of the new cultivar plants were distinct from 'White Wing' in that the former produced almost one fold more leaves than the latter.

The new cultivar 'Icicle' was compared to selected *Caladium* cultivars regarding its susceptibility to *Fusarium* tuber rot. Tubers of the new cultivar 'Icicle' and commercial cultivars 'Candidum' (not patented), 'Carolyn Whorton' (not patented), 'Freida Hemple' (not patented), 'Red Flash' (not patented), and 'White Christmas' (not patented) were surface-sterilized, cut in half, and inoculated with *Fusarium solani* by inserting two pieces of *Fusarium*-colonized carnation leaf segments (Goktepe et al., 2007). Inoculated tuber halves were placed inside egg cartons and incubated at 18° C. under ~100% relative humidity. Tubers were screened with three highly aggressive *F. solani* isolates (13-341, 05-20, and 05-527), and the diameter of the lesion caused by *Fusarium* was measured 2 weeks after inoculation. 'Candidum' (resistant), 'Carolyn Whorton' (highly susceptible), 'Freida Hemple' (high susceptible), 'Red Flash' (moderately resistant), and 'White Christmas' (resistant) had been evaluated previously and they were included as checks (Goktepe et al. 2007).

Table 6 shows the lesion diameters on tuber halves inoculated with one of the three *F. solani* isolates, in comparison with the five commercial *caladium* cultivars with different levels of *Fusarium* tuber rot resistance.

Based on data from the two experiments for *Fusarium* tuber rot, the new cultivar 'Icicle' was resistant to moderately resistant to *Fusarium* tuber rot.

TABLE 6

| | *Fusarium solani* isolates in Experiment 1 | | | *Fusarium solani* isolates in Experiment 2 | | |
|---|---|---|---|---|---|---|
| Cultivar | 13-341 | 05-257 | 05-20 | 13-341 | 05-257 | 05-20 |
| 'Icicle' | 5.7 | 6.4 | 5.0 | 4.7 | 5.5 | 4.1 |
| 'Candidum' | 4.0 | 6.6 | 5.5 | 4.7 | 5.0 | 4.4 |
| 'White Christmas' | 4.4 | 7.1 | 4.9 | 4.7 | 3.9 | 4.1 |
| 'Red Flash' | 6.0 | 9.5 | 6.3 | 6.5 | 6.5 | 6.9 |
| 'Carolyn Whorton' | 7.7 | 9.5 | 6.7 | 5.3 | 9.7 | 6.4 |
| 'Freida Hemple' | 7.0 | 9.7 | 13.0 | 6.5 | 12.9 | 10.2 |

TABLE 6-continued

| Cultivar | Average lesion diameter (mm) | Resistance category |
|---|---|---|
| 'Icicle' | 5.2 | Resistant to moderately resistant |
| 'Candidum' | 5.0 | Resistant (Goktepe et al. 2007). |
| 'White Christmas' | 5.0 | Resistant (Goktepe et al. 2007). |
| 'Red Flash' | 7.0 | Moderately resistant (Goktepe et al. 2007). |
| 'Carolyn Whorton' | 7.6 | Highly susceptible (Goktepe et al. 2007). |
| 'Freida Hemple' | 9.9 | Highly susceptible (Goktepe et al. 2007). |

I claim:

1. A new and distinct *Caladium* plant named 'Icicle' as illustrated and described herein.

* * * * *